(12) United States Patent
Bell et al.

(10) Patent No.: US 6,960,682 B2
(45) Date of Patent: Nov. 1, 2005

(54) PROCESS FOR PRODUCTION OF ACETYL ANHYDRIDES AND OPTIONALLY ACETIC ACID FROM METHANE AND CARBON DIOXIDE

(75) Inventors: Alexis T. Bell, Oakland, CA (US); Sudip Mukhopadhyay, Williamsville, NY (US); Mark Zerella, Berkeley, CA (US); John Glenn Sunley, East Yorkshire (GB); Sander Gaemers, Bishop Burton (GB); Michael James Muskett, Hull (GB)

(73) Assignees: The Regents of the University of California, Oakland, CA (US); BP Chemicals Limited, Middlesex (GB)

(*) Notice: Subject to any disclaimer, the term of this patent is extended or adjusted under 35 U.S.C. 154(b) by 0 days.

(21) Appl. No.: 10/897,769

(22) Filed: Jul. 22, 2004

(65) Prior Publication Data

US 2005/0065364 A1 Mar. 24, 2005

Related U.S. Application Data

(63) Continuation-in-part of application No. 10/627,254, filed on Jul. 24, 2003, now abandoned.

(51) Int. Cl.[7] .......................... C07C 67/36; C07C 51/15
(52) U.S. Cl. ...................... 560/114; 562/550; 562/887
(58) Field of Search ......................... 560/114; 562/550; 562/887, 872

(56) References Cited

U.S. PATENT DOCUMENTS

| | | | |
|---|---|---|---|
| 4,221,712 | A | 9/1980 | Makowski et al. |
| 4,316,828 | A | 2/1982 | Makowski et al. |
| 5,401,876 | A | 3/1995 | Correia et al. |
| 5,659,077 | A | 8/1997 | McFarlan |
| 6,380,426 | B1 | 4/2002 | Kelkar et al. |
| 6,383,977 | B1 | 5/2002 | Karim et al. |
| 6,399,816 | B1 | 6/2002 | Borchert et al. |
| 6,472,558 | B1 | 10/2002 | Key et al. |

FOREIGN PATENT DOCUMENTS

| | | |
|---|---|---|
| GB | 226248 | 12/1924 |
| JP | 10-226665 | * 8/1998 |
| WO | WO 96/05163 A1 | 2/1996 |

OTHER PUBLICATIONS

Martens et al, Tetrahedron, Stereochemistry and Mechanism of Acylation of Acetylenes, 1975, 31(2), pp. 177–183.*

Asadullah, M., et al., "Cobalt catalyzed carboxylation reaction of saturated hydrocarbons with CO in the presence of $K_2S_2O_8$ and TFA under mild conditions," *Tetrahedron Letters*, 1999, pp. 8867–8871, vol. 40.

Asadullah, M., et al., "Calcium–Catalyzed Selective and Quantitative Transformation of $CH_4$ and CO into Acetic Acid" *Angew. Chem. Int. Ed.*, 2000, pp. 2475–2478, vol. 39, No. 14.

Bagno, A., et al., "Superacid–Catalyzed Carbonylation of Methane, Methyl Halides, Methyl Alcohol, and Dimethyl Ether to Methyl Acetate and Acetic Acid," *J. Organic Chem.*, 1990, pp. 4284–4289, vol. 55.

Chepaikin, E., et al., "Functionalisation of methane under dioxygen and carbon monoxide catalyzed by rhodium complexes oxidation and oxidative carbonylation," *Journal of Molecular Catalysis A: Chemical*, 2001, pp. 89–98, vol. 169.

Fujiwara, Y., et al., "Transition metal catalyzed acetic acid synthesis from methane and carbon monoxide," *Studies in Surface Science and Catalysis*, 1998, pp. 349–353, vol. 119.

Jackman, L.M., et al., "Synthesis of Transition–Metal Carboxylato Complexes [1,2]," *Inorganic Chemistry*, 1979, pp. 1497–1502, vol. 18, No. 6.

Kurioka, M., et al., "Palladium–Catalyzed Acetic Acid Synthesis from Methane and Carbon Monoxide or Dioxide," *Chemistry Letters*, 1995, p. 244.

Lin, M., et al., "Direct catalytic conversion of methane to acetic acid in aqueous medium," *Nature*, Apr. 1994, pp. 613–615, vol. 368.

Nakata, K., et al., "Palladium (II) and/or copper (II)–catalyzed carboxylation of small alkanes such as methan and ethane with carbon monoxide," *Journal of Organometallic Chemistry*, 1994, pp. 329–334, vol. 473.

Nishiguchi, T., et al., "Transition Metal Catalyzed Acetic Acid Synthesis from Methane and CO," *Chemistry Letters*, 1992, pp. 1141–1142.

Nizova, G., et al., "Carboxylation of methane with CO or $CO_2$ in aqueous solution catalysed by vanadium complexes," *Chem. Commun.*, 1998, pp. 1885–1886.

Piao, D–G., et al., "An efficient partial oxidation of methane in trifluoroacetic acid using vanadium–containing heteropolyacid catalysts," *Journal of Organometallic Chemistry*, 1999, pp. 116–120, vol. 574.

(Continued)

*Primary Examiner*—Paul A. Zucker
(74) *Attorney, Agent, or Firm*—Townsend and Townsend and Crew LLP

(57) ABSTRACT

Acetyl anhydrides such as acetyl sulfate are produced by a process for comprising contacting methane and carbon dioxide in an anhydrous environment in the presence of effective amounts of a transition metal catalyst and a reaction promoter, and an acid anhydride compound, and optionally an acid. The acetyl anhydride can be contacted with water to produce acetic acid or with an alcohol to produce a product comprising an acetate ester and that may also comprise acetic acid. Optionally, water in stoichiometric amounts or less, with respect to the acetic anhydride, may be fed to a continuous process of this type to produce some acetic acid in situ.

53 Claims, 3 Drawing Sheets

OTHER PUBLICATIONS

Reis, P., et al., "Single–Pot Conversion of Methane Into Acetic Acid in the Absence of CO and with Vanadium Catalysts Such as Amavadine," *Agnew. Chem. Int. Ed.*, 2003, pp. 821–823, vol. 42, No. 7.

Taniguchi, Y., et al., "Advances in Chemical Conversions for Mitigating Carbon Dioxide," *Studies in Surface Science and Catalysis*, 1998, pp. 439–442, vol. 114.

Taniguchi, Y., et al., "Highly Efficient Vanadium–Catalyzed Transformation of CH4 and CO to Acetic Acid," *Organic Letters*, 1999, pp. 557–559, vol. 1, No. 4.

Wilcox et al., "Letter to the Editor: Thermodynamics of light alkane carboxylation," *Applied Catalysis A: General*, 2002, pp. 317–318, vol. 226.

Wilcox, et al., "Direct Synthesis of Acetic Acid from Methane and Carbon Dioxide," *Studies in Surface Science and Catalysis*, 2001, pp. 259–264, vol. 136.

Yin, G., et al., "CU(OAc)$_2$–catalyzed partial oxidation of methane to methyl trifluoroacetate in the liquid phase," *Applied Organometallic Chemistry*, 2000, pp. 438–442, vol. 14.

Zhang, Q., et al., "Reactions between Hydrogen Sulfide and Sulfuric Acid: A Novel Process for Sulfur Removal and Recovery," *Ind. Eng. Chem. Res.*, 2000, pp. 2505–2509, vol. 39.

* cited by examiner

PROCESS FOR PRODUCTION OF ACETYL ANHYDRIDES AND OPTIONALLY ACETIC ACID FROM METHANE AND CARBON DIOXIDE

CROSS-REFERENCE TO RELATED APPLICATIONS

This is a continuation-in-part of application Ser. No. 10/627,254 filed Jul. 24, 2003, now abandoned of Alexis T. Bell et al., similarly entitled "Process For Production Of Acetyl Anhydrides And Optionally Acetic Acid From Methane And Carbon Dioxide". Application Ser. No. 10/627,254 is hereby incorporated herein, in its entirety.

BACKGROUND OF THE INVENTION

This invention relates to the production of acetyl anhydrides, and optionally of acetic acid, and particularly to a process for the production of such substances from methane and carbon dioxide.

The primary process route used today for production of acetic acid is by catalytic reaction of methanol and carbon monoxide. Such a process, typically termed "carbonylation", is described in a number of patents and publications. Rhodium, palladium or iridium-containing catalysts have been found especially useful for conducting this reaction. A recent example of a patent on such a process is U.S. Pat. No. 6,472,558 of Key et al., which describes a process for reaction of methanol (and/or a reactive derivative of methanol such as methyl acetate or dimethyl ether) and carbon monoxide in a liquid reaction composition that comprises methyl acetate, methyl iodide, acetic acid, water and a polydentate phosphine oxide, in addition to the iridium catalyst.

Another process route that has been found useful for the production of acetic acid involves the catalytic oxidation of ethane. Such processes are disclosed, for instance, in U.S. Pat. No. 6,383,977 of Karim et al. and U.S. Pat. No. 6,399,816 of Borchert et al. In the processes described in both patents, a mixed oxide catalyst containing multiple metals is used. Karim et al. discloses catalysts containing molybdenum, vanadium, niobium and palladium, while Borchert et al. discloses containing molybdenum and palladium, plus preferably vanadium, niobium, antimony, nickel and calcium.

Methane is the lowest molecular weight, and simplest in structure, of the hydrocarbons. Because of the existence of large reserves of methane worldwide it has been considered desirable for some time to develop processes to convert methane to more valuable chemicals. Processes for production of acetic acid from methanol represent an ultimate use of methane, but in current commercial practice, the methane first must be converted to methanol. A process that produces acetic acid directly from methane would be more desirable.

A small amount of work has been conducted so far on the direct conversion of methane to acetic acid, for instance by reaction of methane with carbon dioxide. A process for production of acetic acid by such a reaction was disclosed in the 1924 British patent 226,248 of Dreyfus. The patent describes a process involving gas phase reaction of methane with carbon monoxide and/or carbon dioxide in the presence of a catalyst that preferably contains nickel carbonate. Apparently a mixture of acetic acid, acetaldehyde and possibly acetone is obtained. No data on yields or conversions is contained in this patent.

PCT application WO 96/05163 of Hoechst A. G. describes a gas phase reaction of methane and carbon dioxide to produce acetic acid, using a catalyst containing one or more Group VIA, VIIA and/or VIIIA metals. Selectivities of 70–95% based on methane are asserted; however the application contains no exemplary data.

A number of researchers have investigated production of acetic acid by liquid phase carbonylation of methane with carbon monoxide, due to the favorable thermodynamics of this reaction. See, for instance, Bagno, et al. *J. Org. Chem.* 1990, 55, 4284–4289; Lin, et al., *Nature* 1994, 368, 613–615, Chaepaikin, et al., *J. Mol. Catal. A: Chem.* 2001, 169, 89–98; Nishiguchi, et al., *Chem. Lett.* 1992, 1141–1142; Nakata, et al. *J. Organomet. Chem.* 1994, 473, 329–334; Kurioka, et al., *Chem. Lett.* 1995, 244; Fujiwara, et al., *Studies in Surface Science and Catalysis* 1998, 119, 349–353; Taniguchi, et al., *Org. Lett.* 1999, 1(4), 557–559; Asadullah, et al., *Tetrahedron Lett.* 1999, 40, 8867–8871; and Asadullah, et al., *Chem. Int. Ed.* 2000, 39(14), 2475–2478.

Kurioka et al. (1995, supra) also reported a liquid phase experiment in which methane was reacted with carbon dioxide in the presence of palladium acetate, cupric acetate, potassium persulfate and trifluoroacetic acid, reportedly producing acetic acid. The yield was said to have been 1650% (based on the palladium). This work was continued and further reported on by Taniguchi et al., *Studies in Surface Science and Catalysis* 1998, 439–442. That publication described a series of experiments in which methane and carbon dioxide were reacted in the presence of catalysts, primarily vanadium-containing catalysts such as vanadium $(acac)_2$ [acac=acetylacetonate], sodium metavanadate, and vanadium pentoxide, and in the presence of liquids including pure trifluoroacetic acid ("TFA") and aqueous solutions of TFA, hydrochloric acid, sulfuric acid, and sodium hydroxide, as well as simply in water. The best results were obtained in a system that contained only TFA; the worst results were with water alone.

Taniguchi et al. (1998) hypothesized that the acetic acid was produced by reaction of methane and carbon dioxide, but subsequent work by others (and by us) showed that this was not correct; in the Taniguchi et al. work the acetic acid would have been produced primarily if not entirely by reaction of methane and TFA, with concomitant production of one mole of fluoroform for each mole of acetic acid produced by this reaction. TFA, however, is an expensive feedstock for the production of acetic acid. In addition, it is difficult to reconvert the fluoroform byproduct to TFA for recycle or reuse.

Nizova et al., *Chem. Commun.* 1998, 1885 reported results of reactions of methane with carbon monoxide in aqueous systems to produce acetic acid. The authors mention that they had also produced acetic acid by reaction of methane and carbon dioxide in an aqueous system, in the presence of a sodium metavanadate/pyrazine-2-carboxylic acid catalyst. However, the yield (based on methane) appears to have been quite low and pressures rather high (50 bar). Piao et al., *J. Organomet. Chem.* 1999, 574, 116–120 and Yin et al., *Appl. Organomet. Chem.* 2000, 14, 438–442 reported on catalytic partial oxidation of methane to methyl trifluoroacetate, in the presence of trifluoroacetic acid and a small amount of trifluoroacetic acid anhydride, but with no CO or $CO_2$ present. More recently, Reis et al., *Angew. Chem. Int. Ed.* 2003, 42, 821 described production of acetic acid from methane in a single-pot reaction, with trifluoroacetic acid and various vanadium-containing catalysts, notably amavadine, $Ca[V[ON(CH(CH_3)COO)_2]_2]$, but in the absence of carbon dioxide.

It would be desirable to provide a process for production of acetic acid more directly from methane, and particularly from a process that involves methane and carbon dioxide rather than carbon monoxide since carbon dioxide is relatively cheap, and additional oxygen is not needed. A process conducted under relatively mild conditions, adaptable to industrial use rather than a laboratory curiosity, and with good conversions and/or yields, would be highly desirable.

An improved process for the production of acetyl anhydrides also would be desirable. An acetyl anhydride compound can be defined as a compound, which upon reaction with water liberates acetic acid and another non-hydrohalogenoic acid. Alternatively an acetyl anhydride compound may be described as a compound in which the hydroxy group of acetic acid has been replaced with the anion of a non-hydrohalogenoic acid. Acetyl sulfate is one example of an acetyl anhydride. It typically is produced by reacting acetic anhydride with sulfuric acid and has a number of uses, for instance as a sulfonating agent and as a chemical intermediate.

BRIEF SUMMARY OF THE INVENTION

This invention relates to a process for producing an acetyl anhydride comprising:

contacting methane and carbon dioxide in an anhydrous environment in the presence of effective amounts of a transition metal catalyst and a reaction promoter, an acid anhydride compound, and optionally an acid, to produce a product comprising the acetyl anhydride.

In addition, the invention relates to a process for producing a product comprising acetic acid from methane and carbon dioxide comprising producing an acetyl anhydride as above and reacting the product of this step with water.

In another aspect, the invention relates to a process for producing a product comprising an acetate ester by reacting the acetyl anhydride-containing product with an alcohol. Alternatively, the acetyl anhydride could be hydrogenated to produce products comprising ethanol, ethyl bisulfate, ethyl acetate, etc., depending on the non-acetyl component of the anhydride.

Acetyl anhydrides produced as above may be novel compounds and thus form another aspect of this invention.

In a further embodiment, the invention also comprises the step of recovering acetic acid from the reaction product of the acetyl anhydride and water, or recovering the acetate ester from the reaction product of the acetyl anhydride and alcohol.

DETAILED DESCRIPTION OF THE INVENTION

Figure 1:
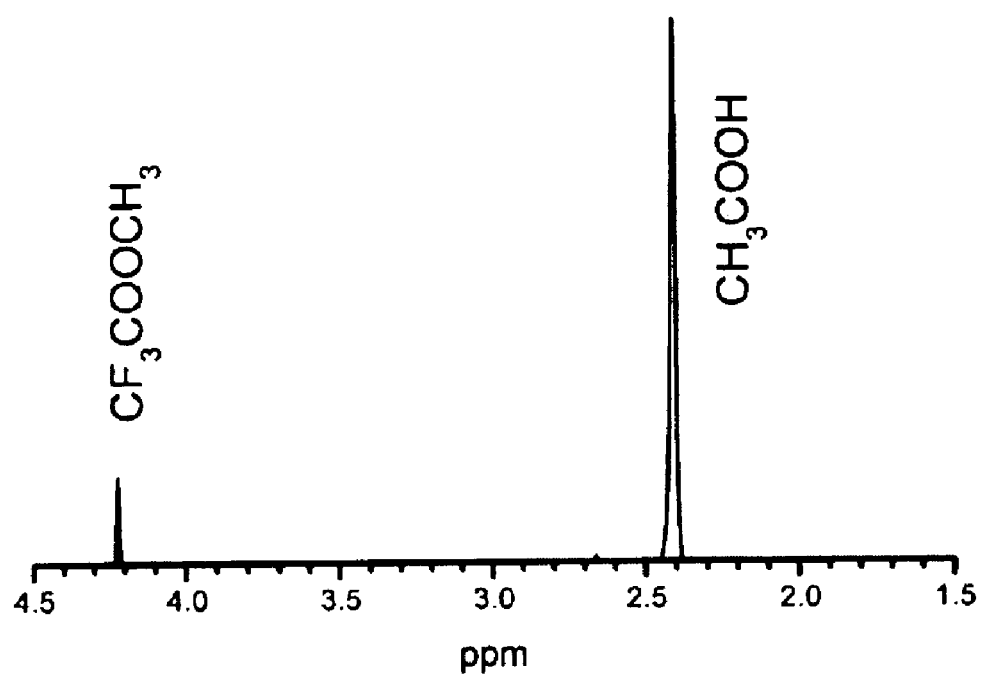
FIG. 1 depicts $^1$H NMR analysis of a product obtained by contacting methane, carbon dioxide, trifluoroacetic acid and trifluoroacetic anhydride, then contacting the product with water.

This invention comprises a process for producing an acetyl anhydride comprising contacting methane and carbon dioxide in an anhydrous environment in the presence of effective amounts of a transition metal catalyst and a reaction promoter, and an acid anhydride compound, and optionally an acid, to produce a product comprising the acetyl anhydride.

The invention further comprises a process for producing a product comprising acetic acid, preferably in two steps, comprising:

(a) contacting methane and carbon dioxide in an anhydrous environment in the presence of effective amounts of a transition metal catalyst and a reaction promoter, and an acid anhydride compound, and optionally an acid, to produce a product comprising an acetyl anhydride; and (b) contacting the reaction product of step (a) with water.

In a further embodiment, the invention also comprises the step of:

(c) recovering acetic acid from the product of step (b).

In another embodiment the invention comprises a process for the production of a product comprising an acetate ester comprising:

(a) contacting methane and carbon dioxide in an anhydrous environment in the presence of effective amounts of a transition metal catalyst and a reaction promoter and an acid anhydride compound, and optionally an acid, to produce a product comprising an acetyl anhydride; and (b) reacting the product of step (a) with an alcohol to produce a product comprising an acetate ester.

The product of step (b) may also comprise acetic acid.

The invention also comprises a process as above, and additionally:

(c) recovering the acetate ester from the product of step (b), and/or recovering acetic acid from the product of step (b).

In the process of this invention, methane and carbon dioxide are contacted, in the presence of a transition metal catalyst, a reaction promoter and an acid anhydride compound, and optionally an acid. The term "acid anhydride compound" as used herein refers generally to a compound that reacts with water to produce an acid. More particularly, for use in the processes of this invention, an acid anhydride must be capable of maintaining the reaction environment in an anhydrous state during the contact of the methane and the carbon dioxide. Acid anhydrides suitable for use in the processes of this invention include, for example, sulfur trioxide, sulfur dioxide, trifluoroacetic acid anhydride, trifluoromethanesulfonic acid anhydride, anhydrides of other sulfonic acids such as fluorosulfonic acid anhydride, fluoromethanesulfonic acid anhydride, methanesulfonic acid anhydride, etc., NO, $NO_2$, $N_2O_5$, $P_2O_5$, $SeO_3$, $As_2O_5$, $TeO_3$, and $B_2O_3$. Some acid anhydrides, such as anhydrides of longer chain carboxylic acids, might not be suitable for use in the processes of this invention, however, as they contain secondary methylene groups that could interact with the reaction promoter.

The term "maintaining the reaction environment in an anhydrous state" means that the overall reaction environment in the acetyl anhydride-formation step is maintained overall in an anhydrous state. However, as discussed below, some water may be present in the reaction zone for a relatively brief time.

The methane, carbon dioxide, and other materials preferably are contacted in the presence of an acid that on the one hand acts as a solvent but that may also participate as a reagent in the process. Suitable acids include organic acids such as trifluoroacetic, fluorosulfonic, methanesulfonic, fluoromethanesulfonic, and trifluoromethanesulfonic acids, and inorganic acids such as sulfuric, sulfurous, nitric, nitrous, phosphoric, phosphorous, superphosphoric, and boric acids, as well as selenium- and tellurium-containing analogs of the sulfur-containing acids. Preferably the acid is the corresponding acid of the acid anhydride compound used, e.g., when the acid anhydride compound is trifluoroacetic acid anhydride the reaction is conducted in the presence of trifluoroacetic acid, and when the acid anhydride compound is sulfur trioxide the acid is sulfuric acid, or in that case, more preferably fuming sulfuric acid is used to supply both the acid and the anhydride. Mixtures of acid anhydride compounds or of acids may be used, if desired.

In general, the molar ratios of the three substances (methane: $CO_2$: acid anhydride compound) are from about 0.5:1:1 to about 1:6:10, preferably from about 1:1:1 to about 1:2:2 respectively. The amount of methane generally ranges from about 10 to about 50 mmol (from about 1 to about 5 mol/dm$^3$, assuming all the methane enters the liquid phase). The amount of carbon dioxide generally ranges from about 5 to about 60 mmol (from about 0.5 to about 6 mol/dm$^3$, assuming all the $CO_2$ enters the liquid phase). In general, this reaction is conducted at a temperature of from about 10 to about 200° C., preferably from about 60 to about 100° C., and for a time of from about 2 to about 48 hours, preferably from about 10 to about 20 hours. The process can be either a batch or continuous process, but is preferably a continuous process. The total pressure of the reaction is suitably in the range 5 barg to 200 barg. The partial pressure of methane is suitably in the range 2.5 barg to 100 barg, and the partial pressure of carbon dioxide is suitably in the range 2.5 barg to 100 barg.

The liquid phase initially comprises the acid anhydride compound and optionally the acid. The acid anhydride compound is present in an amount constituting from about 1% to about 100% of the liquid reaction composition, excluding catalysts and reaction promoters (i.e., if no acid is present, the anhydride is the sole initial liquid component in the process, not including catalyst and reaction promoter). If an acid is used in the process, it is present in the liquid reaction composition in an amount of from about 0.1% to about 99% by weight, preferably from about 1% to about 80% by weight. The acid concentration range is suitably chosen depending on the acid and acid anhydride compound used in the processes. The use of a higher amount of acid may be desirable in order to improve solubility of a particular catalyst and/or promoter in the liquid reaction composition. The acid should be used in as dry a state as practicable.

Also present at this stage are a catalyst and a reaction promoter.

Catalysts suitable for use in this process are transition metal catalysts, particularly compounds of vanadium, chromium, tantalum and niobium. Preferably the transition metal catalyst is a vanadium-containing catalyst such as those known in the art to catalyze reactions between methane and carbon dioxide. A preferred catalyst is vanadyl acetylacetonate, $VO(acac)_2$, where "acac" represents the group $CH_3COCHCOCH_3$. Other suitable vanadium-containing catalysts include sodium metavanadate, $NaVO_3$, vanadium trioxide, vanadium pentoxide, and heteropolyacid catalysts containing vanadium and other metallic and/or non-metallic elements such as phosphorus, silicon, molybdenum and tungsten. Suitable heteropolyacid catalysts are disclosed in Taniguchi et al (1998) and Piao et al. (1999), both supra. Still other suitable catalysts are the vanadium-containing catalysts disclosed in Reis et al. (2003), supra, i.e.:

[VO(N(CH$_2$CH$_2$O)$_3$)],
[VO(N(CH$_2$CH$_2$O)$_2$(CH$_2$COO)],
Ca[V(ON(CH(CH$_3$)COO)$_2$)$_2$],
Ca[V(ON(CH$_2$COO)$_2$)2],
[VO(maltolate)$_2$] (maltolate is the basic form of 3-hydroxy-2-methyl-4-pyrone),
[VO(HOCH$_2$CH$_2$N(CH$_2$CO$_2$)$_2$)],
[VO(CF$_3$COO)$_2$],
[VO(CF$_3$SO$_3$)$_2$], and
VOSO$_4$.

Preferred catalysts of chromium, tantalum and niobium include analogous substances such as the acetylacetonates, oxides, salts of acids whose anions contain the metal (e.g., chromates), and heteropolyacid catalysts containing them.

In general, the catalyst is used in an amount of from about 0.05 mmol to about 0.5 mmol (from about 0.005 to about 0.05 mol/dm$^3$). The molar ratio of methane to catalyst is about 150:1.

Also used in the process is a reaction initiator, that is, a compound that assists in commencement of the reaction through free-radical initiation or other mechanism. Most of the well-known and commonly used reaction initiators may be employed in this process, providing they do not react with other components to form side products or are otherwise undesirable. The preferred initiator is potassium peroxysulfate, $K_2S_2O_8$. Other suitable initiators include $K_4P_2O_8$, calcium dioxide, urea-hydrogen peroxide and m-chloroperbenzoic acid. In general, the initiator is used in an amount of from about 0.5 to about 20 mmol (from about 0.05 to about 2 mol/dm$^3$), preferably from about 3.5 to about 3.7 mmol (from about 0.35 to about 0.37 mol/dm$^3$).

The overall reaction taking place in this process can generally be depicted as $$CH_4 + CO_2 + XO_n \rightarrow CH_3C(O)-O-XO_nH$$

where $XO_n$ is a binary acid anhydride compound, for example $SO_3$, and where the acid form of the binary anhydride is optionally used as the solvent for the reaction, or it can be depicted as $$CH_4 + CO_2 + Z_2O \rightarrow CH_3C(O)-O-Z + ZOH$$

where $Z_2O$ is an acid anhydride compound and where ZOH is an oxygen-containing acid compound, which is optionally used as the solvent for the reaction.

For example, the overall reaction taking place in this process can be depicted as $$CH_4 + CO_2 + H_2S_2O_7 \rightarrow CH_3C(O)-O-SO_3H + H_2SO_4$$

where fuming sulfuric acid ($H_2S_2O_7$) is used in the process, which may be alternatively written as $$CH_4 + CO_2 + SO_3 \rightarrow CH_3C(O)-O-SO_3H$$

(i.e. when fuming sulfuric acid is described as $H_2SO_4$ plus $SO_3$), and $$CH_4 + CO_2 + (CF_3SO_2)_2O \rightarrow CH_3C(O)-O-SO_2CF_3 + CF_3SO_3H$$

where trifluoromethanesulfonic anhydride is used, optionally in the presence of trifluoromethanesulfonic acid.

The product of this process, still in an anhydrous environment, is a mixed anhydride of acetic acid and the acid anhydride compound and/or a mixed anhydride of acetic acid and the acid, if an acid is also used in the process. We term this mixed anhydride an "acetyl anhydride".

If sulfuric or fuming sulfuric acid is used to produce the acetyl anhydride, the product of the reaction is generally also known as acetyl sulfate, which typically is used as a sulfonating agent or as a chemical intermediate. For example, it can be hydrogenated to provide ethanol, ethyl acetate or ethyl bisulfate. Reaction of acetyl sulfate with alcohols produces alkyl acetates and sulfuric acid. Acetyl sulfate is generally produced by reacting acetic anhydride with sulfuric acid; consequently step (a) of the process may serve as an alternate process for producing acetyl sulfate. The acetyl anhydride resulting from a process in which trifluoromethanesulfonic acid is used, or its anhydride is used without the acid, is a novel compound, having the formula $CH_3C(O)-O-SO_2CF_3$, and forms an aspect of this invention. Subsequent reaction of it with water produces acetic acid and trifluoromethanesulfonic acid.

The addition of water to the acetyl anhydride is generally performed at a temperature of from about 0 to about 100° C., preferably from about 30 to about 60° C., and is exothermic. The resulting product is a mixture of acetic acid and the acid used in the acetyl anhydride production, or of acetic acid and the acid anhydride compound, if no acid is employed. The product may also contain small amounts of by-products such as the methyl ester of the starting acid. The acetic acid may readily be separated from the reaction products by techniques such as azeotropic distillation or membrane separation. The other acid may conveniently be recycled to the acetyl anhydride production step.

The process may be run as a continuous or batch process, with appropriate apparatus. If run as a continuous process, water for hydrolysis of the acetyl anhydride may be fed to the reactor, concurrently with methane and carbon dioxide, providing the amount of water is such that the overall reaction environment remains anhydrous. The amount of water thus fed to the process would be at most equal to, and is preferably below, the stoichiometric amount with respect to the acid anhydride used in the process, so that the acid anhydride functions to maintain the process in an overall anhydrous condition. When less than a stoichiometric amount of water is used, the reaction product will be a mixture of acetic acid and the relevant acetyl anhydride. The latter can be converted to acetic acid by subsequent hydrolysis. In a continuous process, promoter and/or catalyst may also be continuously fed, to provide a fresh supply and maintain productivity.

When some water is introduced, the overall reaction becomes, for instance:

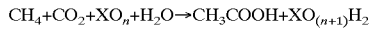

or

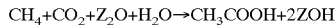

One advantage of running the process in this manner is that acetic acid is produced continuously in a single step. A further advantage is that there is no water to separate from the acetic acid product by distillation or other means, which is expensive and requires energy. In addition, the concentration of acetyl anhydride compound in the reaction medium can be kept to a low level. This can be desirable as acetyl anhydride compounds are known to react to give undesirable polymeric materials (tars), which can cause process complications.

Similarly, if the acetyl anhydride is to be reacted with an alcohol to produce a product comprising an acetate ester, the alcohol may be fed to the reactor concurrently with the methane and carbon dioxide, optionally with feeding water as well. In such an operation the ester may be recovered from the reaction products by techniques such as azeotropic distillation or membrane separation. The products of such a reaction usually also include acetic acid and/or esters of the other acid component of the acetyl anhydride (e.g. trfluoroacetates, trifluoromethanesulfonates, etc.). The proportions of these products would depend on factors such as reaction stoichiometry, the nature of the reacting compounds, and the like. Accordingly, acetic acid and/or esters of the other acid could also be recovered from the products of this step, if desired.

EXAMPLES

The following examples are presented as representative of the invention. However, the invention is not limited thereby, as those skilled in the art would readily recognize variants and modifications of the processes as being within the nature and scope of this invention.

General Procedure

In a typical reaction, $Ch_4$ and $CO_2$ were reacted at 85° C. in a high pressure, glass-lined autoclave. $K_2S_2O_8$ and a small amount of VO(acac)2 were dissolved in an anhydrous acid and its corresponding anhydride (fuming sulfuric acid, $H_2SO_4SO_3$, a mixture of $H_2SO_4$ and $SO_3$; $CF_3SO_3H$ and trifluoromethanesulfonic acid anhydride; trifluoroacetic acid and its anhydride, respectively). Reactions were carried out for 16 h. Upon completion of the reaction, 2 g of water were added to the liquid phase in order to hydrate any anhydrides. The acetic acid thus formed was identified and quantified $^1HNMR$.

To prepare acetic acid from fuming sulfuric acid or a combination of trifluoromethanesulfonic acid and its anhydride, 3.7 mmol (0.37 mol/dm$^3$) $K_2S_2O_8$, 0.16 mmol (1.6×10$^{-2}$ mol/dm$^3$) VO(acac)$_2$, and either 37.5 mmol (3.75 mol/dm$^3$) of $SO_3$ or 10.6 mmol (1.06 mol/dm$^3$) of trifluoromethanesulfonic acid anhydride were charged to a 100 ml glass lined Parr autoclave, together with a small Teflon coated magnetic stir bar. For the preparation of acetic acid using a combination of trifluoroacetic acid and its anhydride, the amounts used were 3.7 mmol $K_2S_2O_8$, 0.16 mmol VO(acac)$_2$, 10.0 g trifluoroacetic acid and 3.0 g of its anhydride. The solvent was chilled to 5–8° C. during these additions to minimize the thermal decomposition of $K_2S_2O_8$. The reactor was then purged with $N_2$ to expel the air out of the system. It was then pressurized first with 120 psig $CO_2$ and then finally with 80 psig methane from adjacent connecting cylinders. The reactor was heated to 85° C. under stirring and maintained for 16–17 h. After that time, the reactor was quenched with ice and opened to collect the reaction mixture. Then 2.0 g of water were slowly added to the mixture, which was then filtered. $^1H$ NMR analysis was then conducted. The results for the reaction using trifluoroacetic acid/anhydride are given in FIG. 1; those for fuming sulfuric acid are given in FIG. 2(a). $D_2O$ was used in a capillary as the lock reference. The corresponding chemical shifts for acetic acid was 2.3 ppm to 2.4 ppm, depending on the concentration of acetic acid in the mixture.

Figure 2:
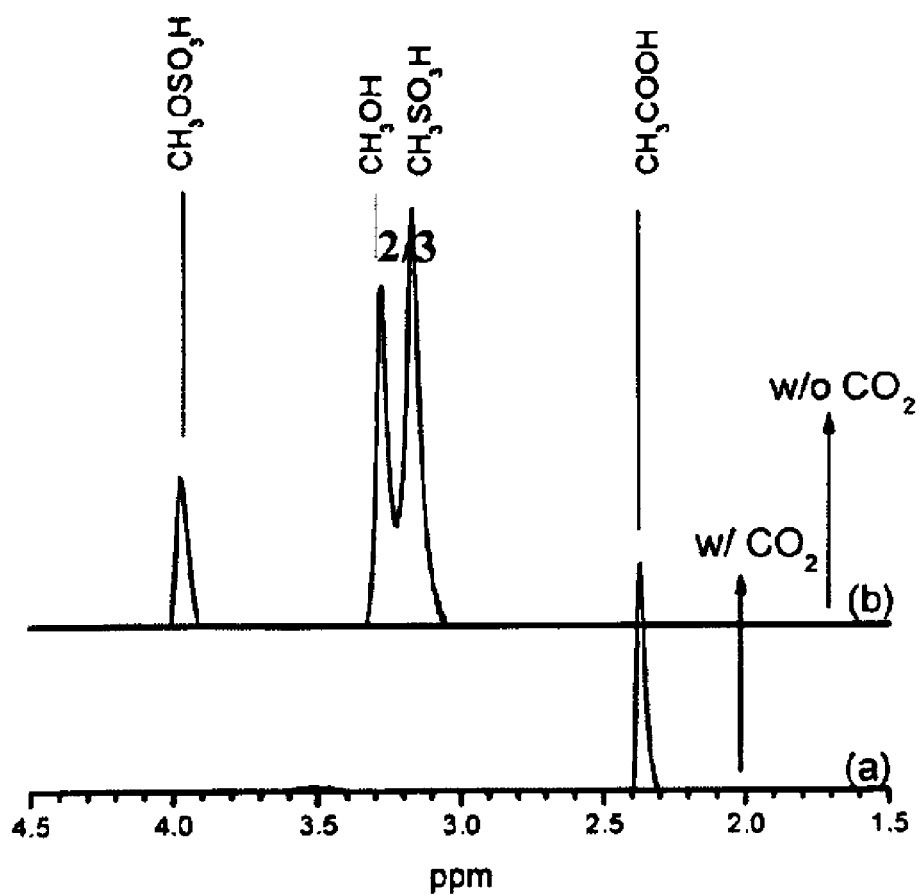
FIG. 2 depicts $^1$H NMR analysis of a product produced by contacting methane, carbon dioxide and fuming sulfuric acid, then contacting the product with water.

Table 1 shows the effect of the starting acid on the conversion of $CH_4$ to acetic acid. The highest conversion (16%) was obtained with trifluoroacetic anhydride and trifluoroacetic acid. Approximately 7% conversion of $CH_4$ to acetic acid was obtained when fuming sulfuric acid was used, and 13% conversion when trifluoromethanesulfonic acid anhydride and trifluoromethanesulfonic acid were used. Small amounts of methyl esters of the starting acids were produced as byproducts in each reaction. To ensure that any CO or $CO_2$ produced by the oxidation of $CH_4$ by $K_2S_2O_8$ under the reaction conditions was not responsible for acetic acid formation, a blank reaction was performed in the absence of $CO_2$. $^1H$ NMR analysis of the product is shown in FIG. 2(b). Only byproducts were detected. The absence of an acetic acid peak in the $^1H$ NMR spectrum demonstrates clearly that the only source of $CO_2$ is that which was originally supplied to the reactor. The excess water added to the mixture after completion of the reaction enables the hydrolysis of byproduct $CH_3OSO_3H$ to methanol and sulfuric acid.

TABLE 1

Direct reaction of $CH_4$ and $CO_2$ with different acid anhydride compounds in the presence of various acids

| Acid | % conversion, $CH_4$ to acetic acid | Byproduct |
|---|---|---|
| $CF_3COOH^a$ | 16 | $CF_3COOCH_3$ |
| $H_2SO_4^b$ | 7 | $CH_3OSO_3H$ |
| $CF_3SO_3H^c$ | 13 | $CF_3SO_3CH_3$ |

Reaction conditions: $CH_4$, 80 psig; $CO_2$, 120 psig; $K_2S_2O_8$, 1 g (3.7 mmol); VO(acac)$_2$, 0.043 g (0.16 mmol); solvent, 10.0 g; 85° C.; 16 h.
[a]Trifluoroacetic acid anhydride, 3.0 g, was added.
[b]$SO_3$, 3.0 g, was added.
[c]Trifluoromethane-sulfonic acid anhydride, 3.0 g, was added.

Figure 3:
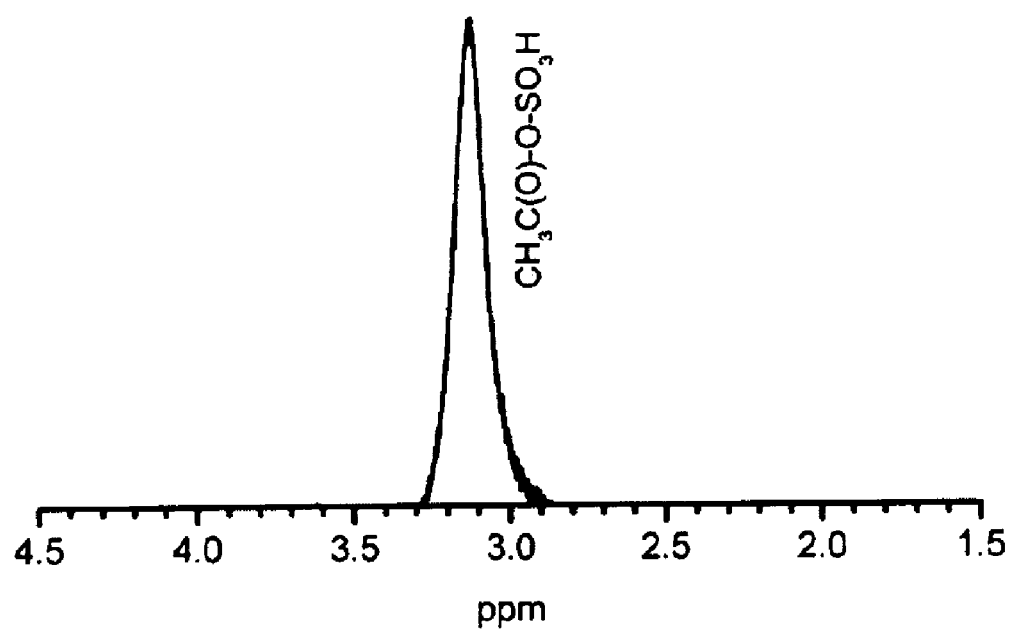
FIG. 3 depicts $^1$H NMR analysis of a product obtained by contacting methane, carbon dioxide and fuming sulfuric acid, before addition of water.

To aid in elucidating the pathway of acetic acid formation from $CH_4$ and $CO_2$ in these acids, the same reaction in sulfuric acid was run, but $^1H$ NMR was performed prior to addition of water to the product mixture. The analytical results are shown in FIG. 3. The product obtained in this reaction was identified as the mixed anhydride of acetic acid and sulfuric acid, $CH_3C(O)$—$OSO_3H$. Upon the addition of water, this mixed anhydride hydrolyzes to produce acetic acid and $H_2SO_4$. The presence of acetic acid was confirmed by distilling a water-acetic acid azeotrope and then analyzing this mixture by $^1H$ NMR and Raman spectroscopy (not shown).

All publications and patent applications cited in this specification are herein incorporated by reference as if each individual publication or patent application were specifically and individually indicated to be incorporated by reference.

The use of the words "a" or "an" herein is intended to include both singular and plural. This, for instance, "an acid", "an anhydride compound", etc. may refer to a single acid or anhydride or a mixture of such compounds Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for producing an acetyl anhydride comprising contacting methane and carbon dioxide in an anhydrous environment in the presence of effective amounts of a transition metal catalyst and a reaction promoter, and an acid anhydride compound, and optionally an acid, to produce a product comprising the acetyl anhydride.

2. A process according to claim 1 further comprising:
   (b) contacting the product comprising the acetyl anhydride with water.

3. A process according to claim 2 further comprising recovering acetic acid from step (b).

4. A process according to claim 1 further comprising:
   (b) contacting the product comprising the acetyl anhydride with an alcohol.

5. A process according to claim 4 further comprising recovering an acetate ester from the product of step (b).

6. A process according to claim 4 further comprising recovering acetic acid from the product of step (b).

7. A process according to claim 1 in which the catalyst is a vanadium-containing catalyst.

8. A process according to claim 7 in which the catalyst is selected from vanadium pentoxide, vanadium trioxide, sodium metavanadate, vanadium-containing heteropolyacid catalysts and vanadyl acetylacetonate.

9. A process according to claim 7 in which the catalyst is vanadyl acetylacetonate.

10. A process according to claim 1 in which the reaction promoter is selected from $K_2S_2O_8$, $K_4P_2O_8$, calcium dioxide, urea-hydrogen peroxide, and m-chloroperbenzoic acid.

11. A process according to claim 10 in which the reaction promoter is $K_2S_2O_8$.

12. A process according to claim 1 in which the acid anhydride compound comprises sulfur trioxide, sulfur dioxide, trifluoroacetic acid anhydride, fluoromethanesulfonic acid anhydride, trifluoromethanesulfonic acid anhydride, fluorosulfonic acid anhydride, methanesulfonic acid anhydride, NO, $NO_2$, $N_2O_5$, $P_2O_5$, $SeO_3$, $As_2O_5$, $TeO_3$, or $B_2O_3$ or a mixture of two or more of the foregoing.

13. A process according to claim 1 in which the acid anhydride compound comprises trifluoroacetic acid anhydride.

14. A process according to claim 1 in which the acid anhydride compound comprises trifluoromethanesulfonic acid anhydride.

15. A process according to claim 1 in which the acid anhydride compound comprises sulfur trioxide.

16. A process according to claim 1 in which the acid anhydride compound comprises fuming sulfuric acid.

17. A process according to claim 1 in which an acid is present during the contacting.

18. A process according to claim 17 in which the acid comprises trifluoroacetic, methanesulfonic, fluorosulfonic, fluoromethanesulfonic, trifluoromethanesulfonic, sulfuric, fuming sulfuric, sulfurous, nitric, nitrous, phosphoric, phosphorous, superphosphoric, or boric acid, or a selenium- and tellurium-containing analog of the sulfur-containing acids, or a mixture of two or more of the foregoing.

19. A process according to claim 17 in which the acid comprises fuming sulfuric acid.

20. A process according to claim 17 in which the acid comprises trifluoroacetic acid.

21. A process according to claim 17 in which the acid comprises trifluoromethanesulfonic acid.

22. A process according to claim 1 in which the acetyl anhydride comprises acetyl sulfate.

23. A process according to claim 1 in which the acetyl anhydride comprises acetyl trifluoroacetate.

24. A process according to claim 1 in which the acetyl anhydride comprises acetyl trifluoromethanesulfonate.

25. A process according to claim 1 in which the temperature is from about 10 to about 200° C.

26. A process according to claim 1 in which the temperature is from about 60 to about 100° C.

27. A process for producing acetic acid comprising:
   (a) contacting methane and carbon dioxide in an anhydrous environment in the presence of effective amounts of a transition metal catalyst and a reaction promoter, and an acid anhydride compound, and optionally an acid, to produce a product comprising an acetyl anhydride; and (b) contacting the product of step (a) with water.

28. A process according to claim 27, further comprising:

(c) recovering acetic acid from the product of step (b).

29. A process according to claim 27 in which the catalyst is a vanadium-containing catalyst.

30. A process according to claim 29 in which the catalyst is selected from vanadium pentoxide, vanadium trioxide, sodium metavanadate, vanadium-containing heteropolyacid catalysts and vanadyl acetylacetonate.

31. A process according to claim 29 in which the catalyst is vanadyl acetylacetonate.

32. A process according to claim 29 in which the reaction promoter is selected from $K_2S_2O_8$, $K_4P_2O_8$, calcium dioxide, urea-hydrogen peroxide and m-chloroperbenzoic acid.

33. A process according to claim 32 in which the reaction promoter is $K_2S_2O_8$.

34. A process according to claim 27 in which the acid anhydride compound comprises sulfur trioxide, sulfur dioxide, trifluoroacetic acid anhydride, trifluoromethanesulfonic acid anhydride, fluoromethanesulfonic acid anhydride, fluorosulfonic acid anhydride, methanesulfonic acid anhydride, NO, $NO_2$, $N_2O_5$, $P_2O_5$, $SeO_3$, $As_2O_5$, $TeO_3$, or $B_2O_3$, or a mixture of two or more of the foregoing.

35. A process according to claim 27 in which the acid anhydride compound comprises trifluoroacetic acid anhydride.

36. A process according to claim 27 in which the acid anhydride compound comprises trifluoromethanesulfonic acid anhydride.

37. A process according to claim 27 in which the acid anhydride compound comprises sulfur trioxide.

38. A process according to claim 27 in which the acid anhydride compound comprises fuming sulfuric acid.

39. A process according to claim 27 in which an acid is present during the contacting.

40. A process according to claim 39 in which the acid comprises trifluoroacetic, fluorosulfonic, methanesulfonic, fluoromethanesulfonic, trifluoromethanesulfonic, sulfuric, fuming sulfuric, sulfurous, nitric, nitrous, phosphoric, phosphorous, superphosphoric or boric acid, or a selenium- or tellurium-containing analog of the sulfur-containing acids, or a mixture of two or more of the foregoing.

41. A process according to claim 39 in which the acid comprises fuming sulfuric acid.

42. A process according to claim 39 in which the acid comprises trifluoroacetic acid.

43. A process according to claim 39 in which the acid comprises trifluoromethanesulfonic acid.

44. A process according to claim 27 in which the acetyl anhydride comprises acetyl sulfate.

45. A process according to claim 27 in which the acetyl anhydride comprises acetyl trifluoroacetate.

46. A process according to claim 27 in which the acetyl anhydride comprises acetyl trifluoromethanesulfonate.

47. A process according to claim 27 in which step (a) is conducted at a temperature of from about 10 to about 200° C.

48. A process according to claim 27 in which the step (a) is conducted at a temperature of from about 60 to about 100° C.

49. A process according to claim 27 further comprising recovering acetic acid from step (b).

50. A process according to claim 39 in which an acid corresponding to the acid used in step (a) is recovered from step (b), and said acid is recycled to step (a).

51. A process for the production of an acetate ester comprising:

(a) contacting methane and carbon dioxide in an anhydrous environment in the presence of effective amounts of a transition metal catalyst and a reaction promoter, and an acid anhydride compound, and optionally an acid, to produce a product comprising an acetyl anhydride; and (b) reacting the product of step (a) with an alcohol to produce a product comprising an acetate ester.

52. A process according to claim 51, further comprising (c) recovering the acetate ester from the product of step (b).

53. A process according to claim 51 in which the product of step (b) further comprises acetic acid, said process further comprising:

(c) recovering acetic acid from the product of step (b).

* * * * *